United States Patent
Kaji et al.

(10) Patent No.: US 9,211,108 B2
(45) Date of Patent: Dec. 15, 2015

(54) ULTRASOUND DIAGNOSTIC IMAGING APPARATUS HAVING PARTICULAR DRIVING SIGNAL CHARACTERISTICS

(71) Applicants: Daisuke Kaji, Hachioji (JP); Yoshihiro Takeda, Hachioji (JP); Kazuya Osada, Hachioji (JP)

(72) Inventors: Daisuke Kaji, Hachioji (JP); Yoshihiro Takeda, Hachioji (JP); Kazuya Osada, Hachioji (JP)

(73) Assignee: KONICA MINOLTA MEDICAL & GRAPHIC, INC., Tokyo (JP)

( * ) Notice: Subject to any disclaimer, the term of this patent is extended or adjusted under 35 U.S.C. 154(b) by 229 days.

(21) Appl. No.: 13/673,353

(22) Filed: Nov. 9, 2012

(65) Prior Publication Data
US 2013/0123632 A1   May 16, 2013

(30) Foreign Application Priority Data

Nov. 11, 2011   (JP) .................. 2011-247363

(51) Int. Cl.
| | |
|---|---|
| A61B 8/00 | (2006.01) |
| A61B 8/14 | (2006.01) |
| G01S 7/52 | (2006.01) |
| G01S 15/10 | (2006.01) |

(52) U.S. Cl.
CPC ... *A61B 8/44* (2013.01); *A61B 8/14* (2013.01); *A61B 8/4444* (2013.01); *A61B 8/4483* (2013.01); *G01S 7/5202* (2013.01); *G01S 15/102* (2013.01)

(58) Field of Classification Search
USPC ........................................ 600/437, 443, 459
See application file for complete search history.

(56) References Cited

U.S. PATENT DOCUMENTS

| | | | |
|---|---|---|---|
| 5,833,614 A | 11/1998 | Dodd et al. | |
| 6,494,841 B1 * | 12/2002 | Thomas et al. | ............... 600/447 |

FOREIGN PATENT DOCUMENTS

JP           07231247 A       8/1995

OTHER PUBLICATIONS

Alan V. Oppenheim, Alan S. Willsky, S. Hamid, "Signals and Systems (2nd Edition)" English | Aug. 16, 1996 | ISBN: 0138147574 | Table 4.2.*

Japanese Office Action (and English translation thereof) dated Jun. 30, 2015, issued in counterpart Japanese Application No. 2011-247363.

* cited by examiner

*Primary Examiner* — Katherine Fernandez
*Assistant Examiner* — Michael Kellogg
(74) *Attorney, Agent, or Firm* — Holtz, Holtz, Goodman & Chick PC

(57) ABSTRACT

Disclosed is an ultrasound diagnostic imaging apparatus including an ultrasound probe which outputs transmission ultrasound waves toward a subject by a driving signal and which outputs received signals by receiving reflection ultrasound waves from the subject and a transmitting unit which generates the transmission ultrasound waves by the ultrasound probe by outputting the driving signal, and the transmitting unit generates the driving signal of square wave having a waveform in which a standard pulse signal where a pulse cycle is 2 T is combined with two first pulse signals of same polarity having a pulse width A (A<T) and a second pulse signal having a pulse width B (B=T−2A), the second pulse signal having a polarity different from the polarity of the first pulse signals.

20 Claims, 5 Drawing Sheets

ULTRASOUND DIAGNOSTIC IMAGING APPARATUS HAVING PARTICULAR DRIVING SIGNAL CHARACTERISTICS

BACKGROUND OF THE INVENTION

1. Field of the Invention

The present invention relates to an ultrasound diagnostic imaging apparatus.

2. Description of Related Art

In conventional ultrasound diagnostic imaging apparatus, ultrasound waves (transmission ultrasound waves) are transmitted toward a subject such as a living object by an ultrasound probe and received ultrasound waves (reflection ultrasound waves) are converted into received signals by an ultrasound probe to display an ultrasound image on the basis of the received signals. The reflection ultrasound waves include information which indicates conditions inside the subject. Therefore, it is important to obtain reflection ultrasound waves of good quality in order to obtain a good quality ultrasound image. Quality of ultrasound image can be improved by performing signal processing and the like on received signals. However, it is preferred that transmission ultrasound waves are good quality innately.

Good quality transmission ultrasound wave means to have great temporal resolution and space resolution. Among those, temporal resolution (resolution in depth direction) can be improved by making the frequency band of transmission ultrasound waves be broad.

In view of the above, U.S. Pat. No. 5,833,614 discloses a technique for adjusting pulse signals by gradually changing pulse width of driving signals (pulse signals) of pulse square wave to obtain second harmonic component that is generated by transmission of ultrasound waves in a subject in the conventional ultrasound diagnostic imaging apparatus.

SUMMARY OF THE INVENTION

Generally, cyclical pulse signals of square wave, represented by the waveform shown in FIG. 8, have frequency characteristics (amplitude, phase) determined according to the cycle. Here, a pulse signal shown in FIG. 8 is a pulse signal which can be expressed by a function f(x) where one cycle is 2 T, and when the waveform of this pulse signal is converted by Fourier transform, it can be expressed as formula (1) shown below. Here, in formula (1), "ω" represents frequency and "i" represents imaginary unit.

Formula 1

$$F[f](\omega) = e^{-i\frac{T}{2}\omega} \cdot \frac{2\sin\frac{T}{2}\omega}{\omega} - e^{i\frac{T}{2}\omega} \cdot \frac{2\sin\frac{T}{2}\omega}{\omega} \tag{1}$$

However, in the invention described in U.S. Pat. No. 5,833,614, it is difficult to output transmission ultrasound waves having the desired frequency characteristic taking the characteristics of the ultrasound probe to be used into consideration, for example, how the function expressed by the formula (1) can be changed to obtain frequency characteristic where the characteristics of the ultrasound probe to be used are taken into consideration is difficult. That is, in order to output transmission ultrasound waves having the desired frequency characteristic, a special frequency designing unit such as to increase or decrease a specific frequency when generating a pulse signal was needed.

The present invention was made in view of the above problem and an object of the present invention is to provide an ultrasound diagnostic imaging apparatus which can output broad transmission ultrasound waves having the desired frequency characteristic.

In order to achieve the above described object, an ultrasound diagnostic imaging apparatus reflecting one aspect of the present invention includes an ultrasound probe which outputs transmission ultrasound waves toward a subject by a driving signal and which outputs received signals by receiving reflection ultrasound waves from the subject and a transmitting unit which generates the transmission ultrasound waves by the ultrasound probe by outputting the driving signal, and the transmitting unit generates the driving signal of square wave having a waveform in which a standard pulse signal where a pulse cycle is 2 T is combined with two first pulse signals of same polarity having a pulse width A (A<T) and a second pulse signal having a pulse width B (B=T−2A), the second pulse signal having a polarity different from the polarity of the first pulse signals.

Preferably, the transmitting unit generates the driving signal so that the two first pulse signals are arranged at positions to be symmetrical along a time line with respect to the second pulse signal.

Preferably, the transmitting unit generated the driving signal by making the pulse width A of the first pulse signals be smaller than the pulse width B of the second pulse signal.

Preferably, the transmitting unit generates the driving signal so that one of the two first pulse signals be at an initial part of the driving signal.

Preferably, the transmitting unit makes the pulse width A of the first pulse signals and the pulse width B of the second pulse be variable.

Preferably, the transmitting unit generates the driving signal of a square driving waveform which is expressed by including the following formula.

Formula 2

$$F[f](\omega) = \tag{2}$$
$$e^{-i\frac{T}{2}\omega} \cdot \frac{2\sin\frac{T}{2}\omega}{\omega} - e^{i\frac{T}{2}\omega} \cdot \frac{2\sin\frac{B}{2}\omega}{\omega} + \left(e^{i\frac{A}{2}\omega} + e^{i\left(\frac{3A}{2}+B\right)\omega}\right) \cdot \frac{2\sin\frac{A}{2}\omega}{\omega}$$

wherein "ω" represents a frequency and "i" represents an imaginary unit.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENT

Figure 1:
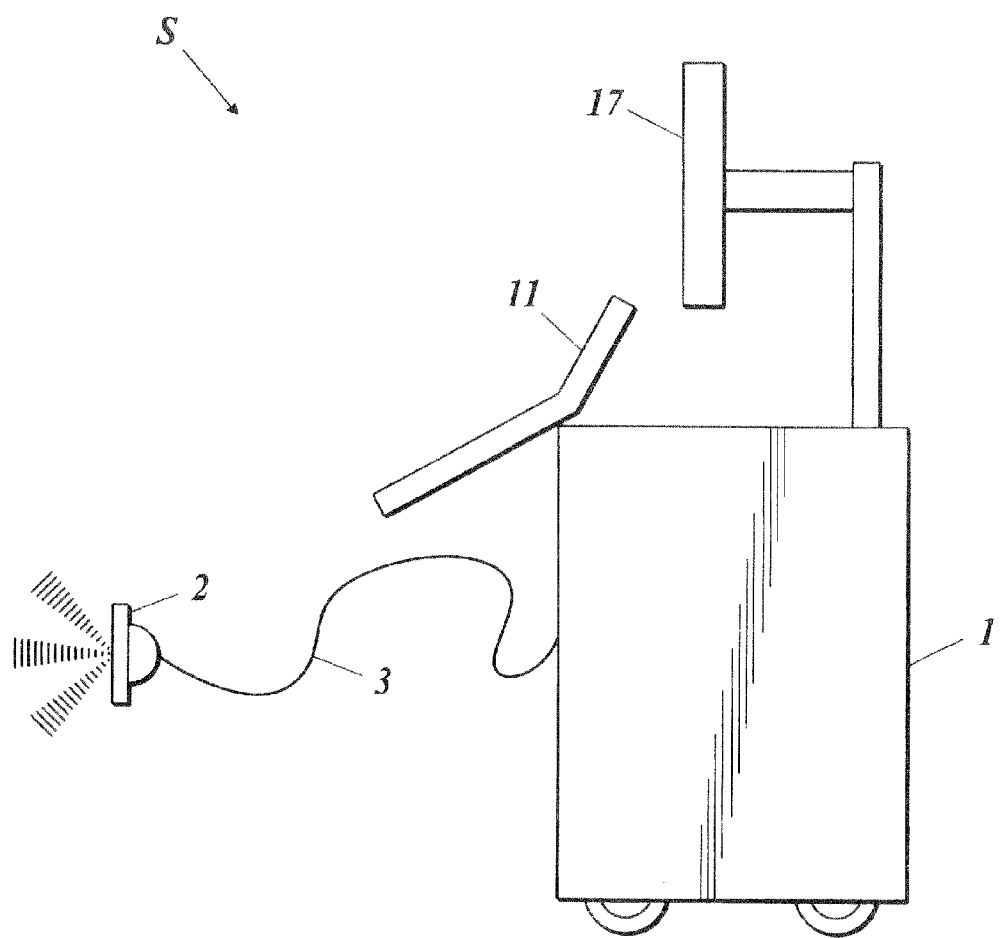
FIG. 1 is a diagram showing an outer configuration of an ultrasound diagnostic imaging apparatus.

Hereinafter, an ultrasound diagnostic imaging apparatus according to an embodiment of the present invention will be described with reference to the drawings. However, the scope of the present invention is not limited to the examples shown in the drawings. In the following description, same references are used for same functions and configuration and their descriptions are omitted.

Figure 2:
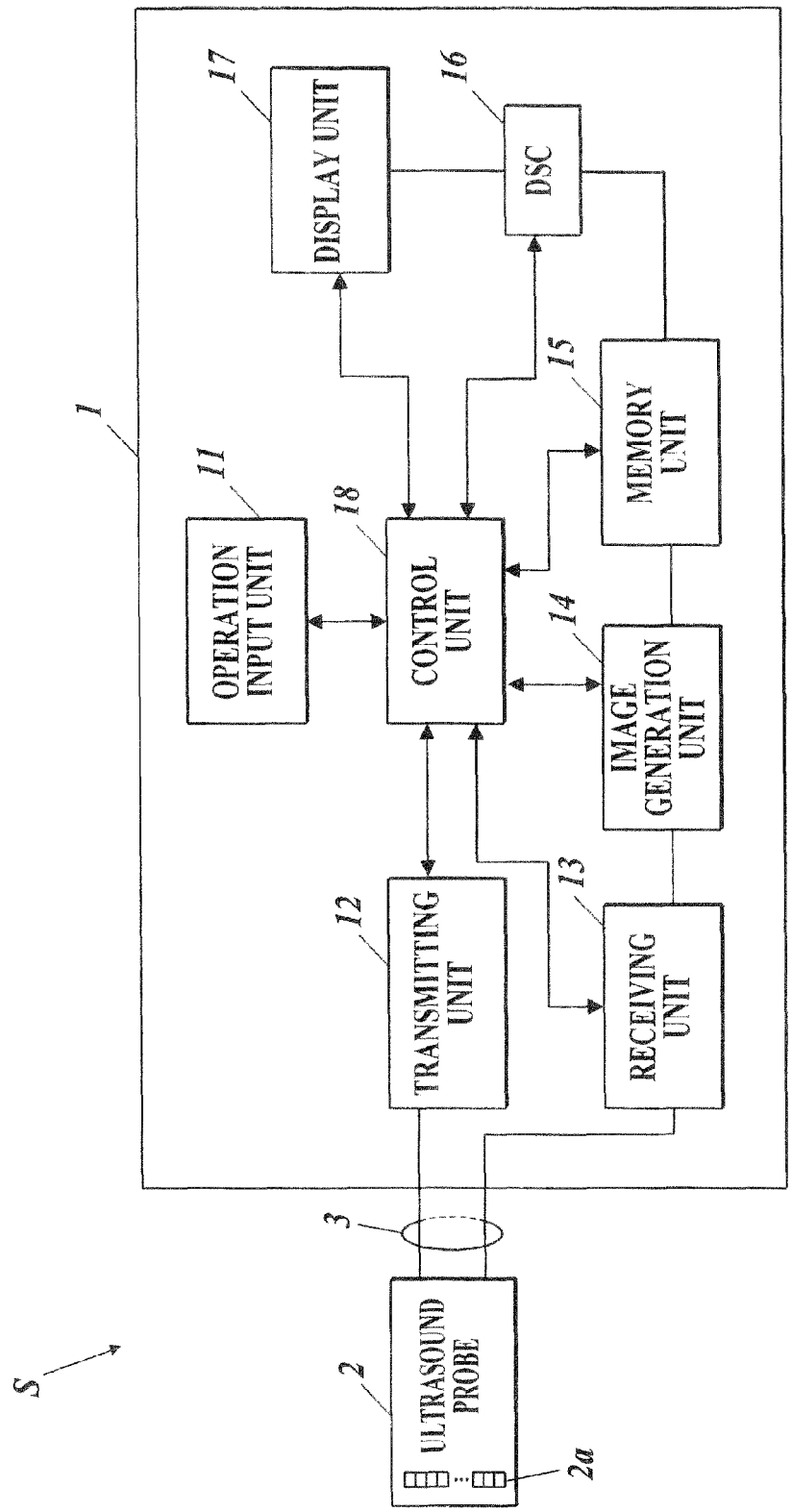
FIG. 2 is a block diagram showing a schematic configuration of the ultrasound diagnostic imaging apparatus.

As shown in FIGS. 1 and 2, the ultrasound diagnostic imaging apparatus S according to the embodiment includes an ultrasound diagnostic imaging apparatus main body 1 and an ultrasound probe 2. The ultrasound probe 2 transmits ultrasound waves (transmission ultrasound waves) toward a subject such as a living object (omitted in the drawing) and receives reflected waves (reflection ultrasound waves: echo) of the ultrasound waves reflected off the subject. The ultrasound diagnostic imaging apparatus main body 1 is connected with the ultrasound probe 2 via a cable 3 and transmits driving signals which are electronic signals to the ultrasound probe 2 to make the ultrasound probe 2 transmit transmission ultrasound waves toward a subject. Further, the ultrasound diagnostic imaging apparatus main body 1 forms an ultrasound image of inside condition of the subject on the basis of received signals which are electronic signals generated by the ultrasound probe 2 according to the reflection ultrasound waves coming from inside of the subject which are received by the ultrasound probe 2.

The ultrasound probe 2 includes transducers 2a formed of piezo-electric devices, and the plurality of transducers 2a are arranged in one dimensional array in an orientation direction, for example. In the embodiment, for example, an ultrasound probe 2 having 192 transducers 2a is used. Here, the transducers 2a may be arranged in two dimensional array. Further, the number of transducers 2a can be set arbitrarily. In the embodiment, a linear scanning type electronic scanning probe is used as the ultrasound probe 2. However, any of an electronic scanning type and a mechanical scanning type can be used. Further, any of a linear scanning type, a sector scanning type and a convex scanning type can be used. Band width of ultrasound probe can be set arbitrarily.

As shown in FIG. 2, the ultrasound diagnostic imaging apparatus main body 1 includes an operation input unit 11, a transmitting unit 12, a receiving unit 13, an image generation unit 14, a memory unit 15, a DSC (Digital Scan Converter) 16, a display unit 17 and a control unit 18, for example.

The operation input unit 11 includes various types of switches, buttons, a track-ball, a mouse, a key board and the like for inputting a command for instructing start of diagnosis and data such as personal information of a subject, and the operation input unit 11 outputs operation signals to the control unit 18.

Figure 3:
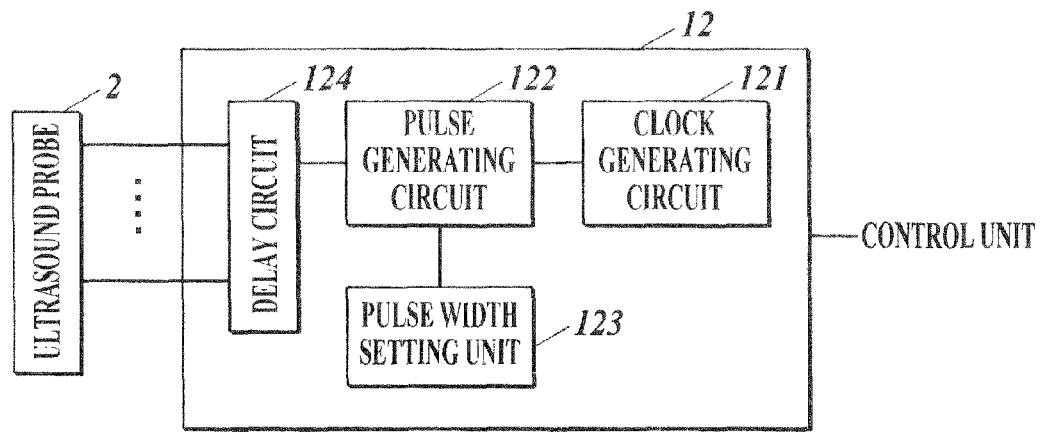
FIG. 3 is a block diagram showing a schematic configuration of a transmitting unit.

The transmitting unit 12 is a circuit to make the ultrasound probe 2 generate transmission ultrasound waves by supplying driving signals which are electronic signals to the ultrasound probe 2 via the cable 3 in compliance with the control of the control unit 18. More specifically, as shown in FIG. 3, the transmitting unit 12 includes a clock generating circuit 121, a pulse generating circuit 122, a pulse width setting unit 123 and a delay circuit 124, for example.

The clock generating circuit 121 is a circuit for generating clock signals which decide transmission timing and transmission frequency of driving signals.

Figure 4:
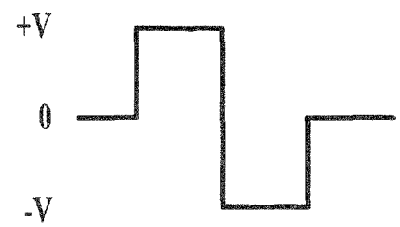
FIG. 4 is a diagram for explaining a driving waveform of a pulse signal.

The pulse generating circuit 122 is a circuit for generating pulse signals as driving signals in predetermined cycles. As shown in FIG. 4, the pulse generating circuit 122 can generate pulse signals of square wave by switching ternary voltage. At this time, amplitude of a pulse signal is set so that positive polarity and negative polarity be the same. However, this is not limitative in any way. Pulse signals may be generated by switching binary voltage.

The pulse width setting unit 123 sets the pulse width of pulse signals which are output from the pulse generating circuit 122. That is, the pulse generating circuit 122 outputs pulse signals of pulse waveform which complies with the pulse width set by the pulse width setting unit 123. For example, pulse width can be changed by an input operation of the operation input unit 11. Further, configuration may be such that the ultrasound probe 2 connected to the ultrasound diagnostic imaging apparatus main body 1 is identified and the pulse width corresponding to the identified ultrasound probe 2 is to be set. Here, setting of pulse width by the pulse width setting unit 123 will be described in detail later.

The delay circuit 124 is a circuit for setting a delay time for each path regarding transmission timing of driving signals, each path corresponding to each transducer, and converging transmission beams formed of transmission ultrasound waves by delaying transmission of driving signals for the set delay time.

The transmitting unit 12 which is configured as described above sequentially switches the plurality of transducers 2a which supply driving signals, shifting by a predetermined numbers for each transmitting and receiving of ultrasound wave in compliance with the control of the control unit 18 and supplies driving signals to the plurality of transducers 2a which are selected to perform output to carry out scanning.

As shown in FIG. 2, the receiving unit 13 is a circuit for receiving received signals which are electronic signals from the ultrasound probe 2 via the cable 3 in compliance with the control of the control unit 18. The receiving unit 13 includes an amplifier, an A/D converting circuit and a phasing addition circuit, for example. The amplifier is a circuit for amplifying the received signals at a predetermined amplification factor which is set in advance for each path corresponding to each transducer 2a. The A/D converting circuit is a circuit for performing analog/digital conversion (A/D conversion) on the received signals which are amplified. The phasing addition circuit is a circuit to adjust time phase by applying a delay time to each path corresponding to each of the transducers 2a with respect to the received signals on which A/D conversion is performed and generate sound ray data by adding (phasing addition) the adjusted received signals.

The image generating unit 14 performs envelope detection processing, logarithmic amplification and the like on the sound ray data from the receiving unit 13 and generates B-mode image data by performing brightness conversion by carrying out gain adjustment and the like. That is, the B-mode image data is data which expresses intensity of the received signals by brightness. The B-mode image data generated in the image generation unit 14 is transmitted to the memory unit 15.

The memory unit 15 is configured by including a semiconductor memory such as DRAM (Dynamic Random Access Memory) or the like, for example, and the B-mode image data transmitted from the image generation unit 14 is stored in frame units. That is, the memory unit 15 can store the B-mode image data as ultrasound diagnosis image data configured in frame units. The ultrasound diagnosis image data stored in the memory unit 15 is read out in compliance with the control of the control unit 18 and is transmitted to the DSC 16.

The DSC 16 converts the ultrasound diagnosis image data which is received from the memory unit 15 into image signals of scanning type of television signals and output the converted image signals to the display unit 17.

As for the display unit 17, a display apparatus such as LCD (Liquid Crystal Display), CRT (Cathode-Ray Tube) display, an organic EL (Electronic Luminescence) display, an inorganic EL display, a plasma display or the like can be applied. The display unit 17 performs displaying of an ultrasound diagnosis image in the display screen according to the image signals output from the DSC 16. Here, printing apparatus or the like such as a printer can be applied instead of a display apparatus.

The control unit 18 includes a CPU (Central Processing Unit), a ROM (Read Only Memory) and a RAM (Random Access Memory), for example. The control unit 18 reads out various types of processing programs such as a system program and the like stored in the ROM and expands them in the RAM, and performs centralized control of operation of each part of the ultrasound diagnostic imaging apparatus S in compliance with the expanded programs.

The ROM is configured by including a non-volatile memory such as a semiconductor and stores a system program corresponding to the ultrasound diagnostic imaging apparatus S, various types of processing programs which are executable on the system program and various types of data, for example. These programs are stored in forms of program code which can be read by a computer, and the CPU sequentially executes operations according to the program codes.

The RAM forms a work area to temporarily store various types of programs which are to be executed by the CPU and data according to such programs.

A driving signal generated by the transmitting unit 12 of the ultrasound diagnostic imaging apparatus S which is configured as described above will be described with reference to FIG. 5.

Figure 5:
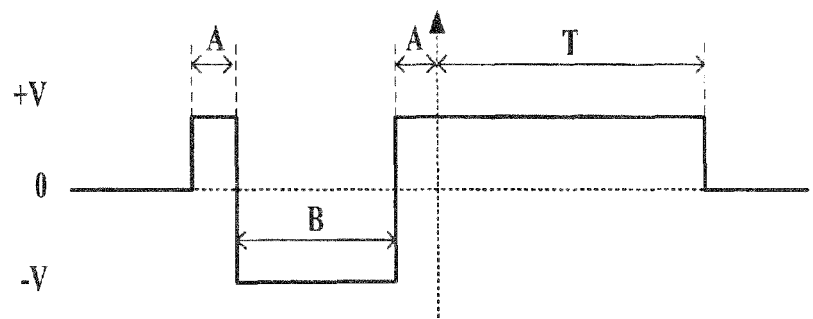
FIG. 5 is a diagram for explaining a waveform of a pulse signal to be transmitted.

FIG. 5 shows an example of preferable waveform of driving signals applied to the transducers 2a of the ultrasound probe 2 used in the embodiment.

That is, the waveform of driving signal shown in FIG. 5 is a waveform where two types of pulse signals having pulse widths which are set in advance are combined with the standard pulse signal where one cycle is 2 T which can be expressed by the function f (x).

More specifically, the pulse width setting unit 123 of the transmitting unit 12 first sets the above mentioned standard pulse signal and sets a pulse signal of polarity (+) having a pulse width A at the start of the standard pulse signal. This pulse signal may be called the first pulse signal. Then, the pulse width setting unit 123 sets a pulse signal of polarity (−) having a pulse width B continuously following the first pulse signal. This pulse signal may be called the second pulse signal. That is, the second pulse signal is pulse signal having a polarity different from that of the first pulse signal. Then, the pulse width setting unit 123 sets the first pulse signal continuously following the second pulse signal. In such way, a transmission pulse signal to be transmitted to the ultrasound probe 2 is generated. That is, the transmission pulse signal is a pulse signal obtained by combining two first pulse signals and one second pulse signal with the standard pulse signal.

Here, the first pulse signals and the second pulse signal may have polarities opposite of those shown in FIG. 5.

Further, it is sufficient that the transmission pulse signal has same waveform as the waveform of the above combination of signals, thus, each signal can be generated individually and then they can be combined.

The transmission pulse signal which is generated as described above is set so that the sum of the pulse widths of two first pulse signals and the pulse width of one second pulse signal (2A+B) is the same as half cycle T of the standard pulse signal. Here, the pulse width A of the first pulse signal and the pulse width B of the second pulse signal can be set arbitrarily within a range where the sum of the pulse widths of two first pulse signals and the pulse width of one second pulse signal be the same as half cycle T of the standard pulse signal.

When Fourier transform of waveform of the transmission pulse signal generated as described above is carried out, it can be expressed as the following formula (2). Here, the transmission pulse signal expressed by the following formula (2) can be expressed by the function f(x) and one cycle thereof is 2 T. Here, in the following formula (2), "ω" represents frequency and "i" indicates imaginary unit.

Formula 2

$$F[f](\omega) = e^{-i\frac{T}{2}\omega} \cdot \frac{2\sin\frac{T}{2}\omega}{\omega} - e^{i\frac{T}{2}\omega} \cdot \frac{2\sin\frac{B}{2}\omega}{\omega} + \left(e^{i\frac{A}{2}\omega} + e^{i\left(\frac{3A}{2}+B\right)\omega}\right) \cdot \frac{2\sin\frac{A}{2}\omega}{\omega} \quad (2)$$

Here, when the pulse width A of the first pulse signals included in the transmission pulse signal is set relatively small, values obtained in the first section and the second section of the above formula (2) are close to the frequency characteristic of the standard pulse signal. At this time, because the pulse width A is small, the value obtained in the third section is to have abroad frequency characteristic where the band covers all the way to the high-frequency side due to the coefficient "{2 sin(A/2)ω}/ω" according to the small pulse width A. As a result, in combination with the value obtained by "e^{i(A/2)ω}+e^{i(3A/2+B)ω}", it can be expected that the peak of frequency will be in high-frequency part. Therefore, by generating the transmission pulse signal as described above, transmission ultrasound waves having a frequency characteristic of having a plurality of peaks (diphasic) can be obtained easily, and further, frequency characteristic of the transmission ultrasound waves can be controlled.

The frequency response characteristic of the ultrasound probe 2 with respect to the transmission pulse signal generated as described above is as shown in FIG. 6. Here, in FIG. 6, "W" indicates frequency characteristic of the transmission pulse signal, "P" indicates frequency response characteristic of the ultrasound probe 2 and "Q" indicates frequency response characteristic of the ultrasound probe 2 with respect to the transmission pulse signal.

Figure 6:
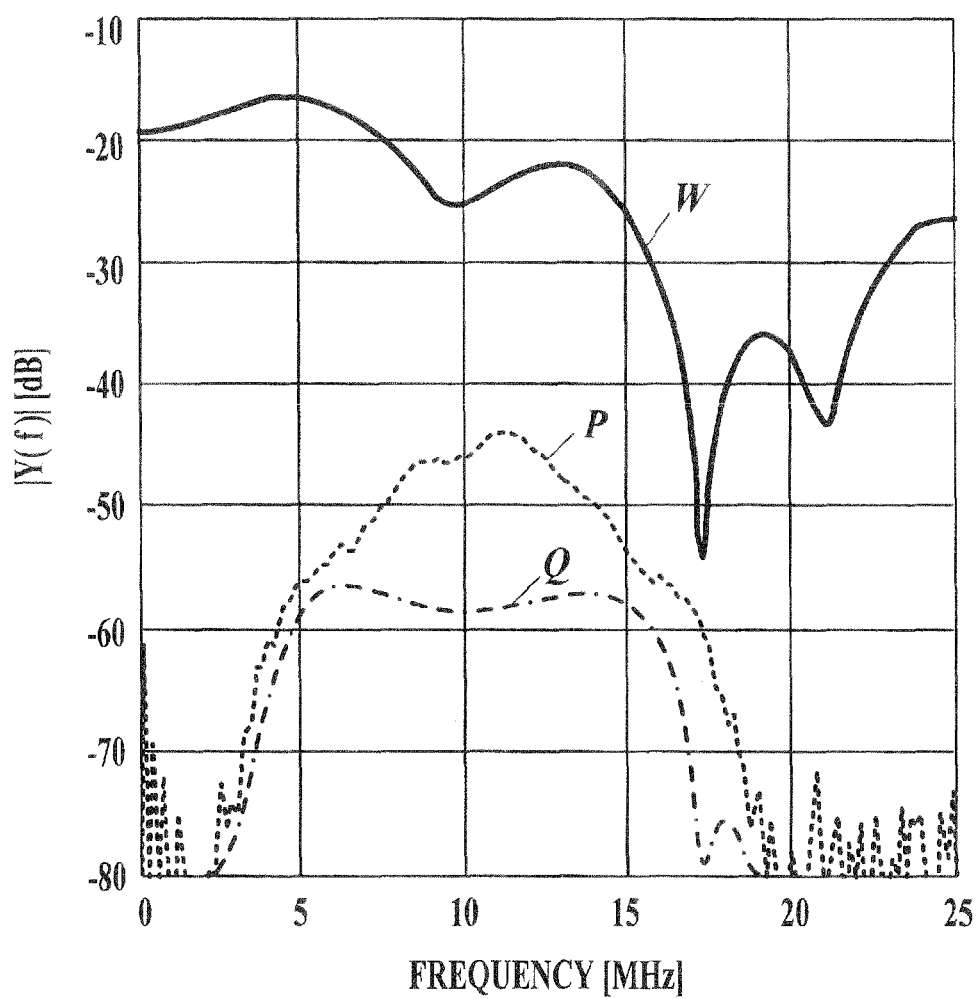
FIG. 6 is a diagram for explaining frequency response characteristic of an ultrasound probe.

As shown in FIG. 6, frequency response characteristic of the ultrasound probe generally forms a bell shape like a normal distribution, and the characteristic becomes lower in high-frequency part and low-frequency part comparing to the peak. On the other hand, when transmission ultrasound waves transmitted from the ultrasound probe can be made to be broad, the transmission ultrasound waves are to have very high locality by becoming short pulses when seen along time axis. That is, if the transmission ultrasound waves can be made to be broad, the transmission ultrasound waves can have a great temporal resolution.

Here, as a method to make the transmission ultrasound waves be broad, a transmission pulse signal having frequency characteristic which is opposite of the frequency response characteristic of the ultrasound probe may be applied to the ultrasound probe. That is, if a transmission pulse signal having high frequency characteristic can be applied to the ultrasound probe at the high-frequency part and the low-frequency part where the frequency response characteristic of the ultrasound probe is low, transmission ultrasound waves can become broad. Such frequency response characteristic is generally diphasic.

In the embodiment, because the transmission pulse signal is generated as described above, diphasic frequency response characteristic can be obtained as shown in FIG. 6 and a broad transmission ultrasound waves according to the characteristic of the ultrasound wave probe, although it is a transmission pulse signal of square waveform, can be designed easily.

Moreover, in the embodiment, the frequency characteristic is described in the above formula (2), and by adjusting the pulse width A of the first pulse signals and the pulse width B of the second pulse signal, positions of the peaks of frequency response characteristic of the ultrasound probe with respect to the transmission pulse signal can be changed to be in a desired frequency band. That is, positions of diphasic peaks which the frequency response characteristic of the ultrasound probe with respect to transmission pulse signal indicates can be controlled. Therefore, for example, an appropriate frequency response characteristic can be obtained according to the frequency response characteristic of the ultrasound probe to be used, and the ultrasound probe can be utilized effectively. At this time, by making the pulse width A of the first pulse signals be smaller than the pulse width B of the second pulse signal, more preferred frequency response characteristic of the ultrasound probe with respect to transmission pulse signal can be obtained.

As described above, according to the embodiment, the ultrasound probe 2 outputs transmission ultrasound waves toward a subject by driving signals and outputs received signals by receiving reflection ultrasound waves reflected off the subject. The transmitting unit 12 makes the ultrasound probe 2 generate transmission ultrasound waves by outputting driving signals. The transmitting unit 12 generates driving signals of square wave having a waveform where the standard pulse signal in which the pulse cycle is 2 T is combined with two first pulse signals of same polarity which are pulse widths A and the second pulse signal which is pulse width B, the second pulse signal having a polarity different from the polarity of the first pulse signal. As a result, the frequency response characteristic of the ultrasound probe with respect to driving signal can be diphasic. Further, driving signal suited for the frequency response characteristic of the ultrasound probe can be designed easily. Therefore, broad transmission ultrasound waves having the desired frequency characteristic can be output easily.

Moreover, according to the embodiment, the transmitting unit 12 generates a driving signal so that two first pulse signals are arranged at positions so as to be symmetry along a time line with respect to the second pulse signal. As a result, driving signal can be designed even more easily.

Furthermore, according to the embodiment, the transmitting unit 12 generates a driving signal by setting the pulse width A of the first pulse signals be smaller than the pulse width B of the second pulse signal. As a result, more preferred frequency response characteristic of the ultrasound probe with respect to driving signal can be obtained.

Further, according to the embodiment, the transmitting unit 12 generates a driving signal so that one of the two first pulse signals be at the initial part of the driving signal. As a result, more preferred frequency response characteristic of the ultrasound probe with respect to driving signal can be obtained.

Moreover, according to the embodiment, because the pulse width A of the first pulse signals and the pulse width B of the second pulse signal can be changed, the transmitting unit 12 can change the positions of peaks which the frequency response characteristic of the ultrasound probe with respect to the driving signal indicates. That is, positions of the diphasic peaks which the frequency response characteristic of the ultrasound probe with respect to driving signal indicates can be controlled. Therefore, for example, appropriate frequency response characteristic according to the frequency response characteristic of the ultrasound probe to be used can be obtained and the ultrasound probe can be utilized effectively.

Here, the description of the embodiment of the present invention is an example of an ultrasound diagnostic imaging apparatus according to the present invention and the present invention is not limited to the description. Detail configuration and detail operation of each functional component which constitutes the ultrasound diagnostic imaging apparatus can be changed arbitrarily.

Figure 7:
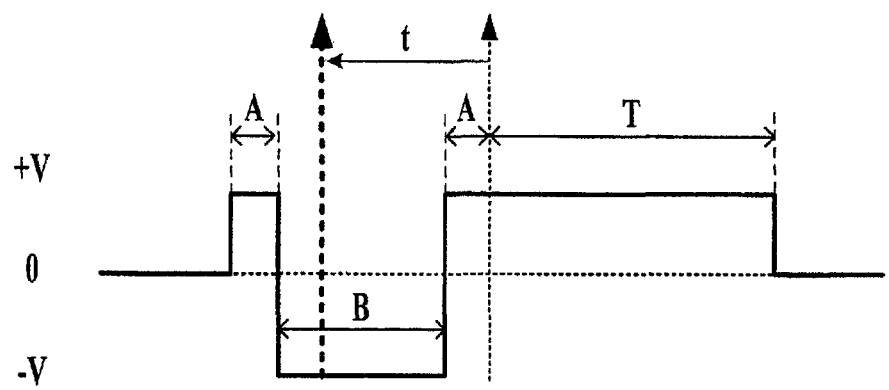
FIG. 7 is a diagram for explaining another example of waveform of a pulse signal to be transmitted.
Figure 8:
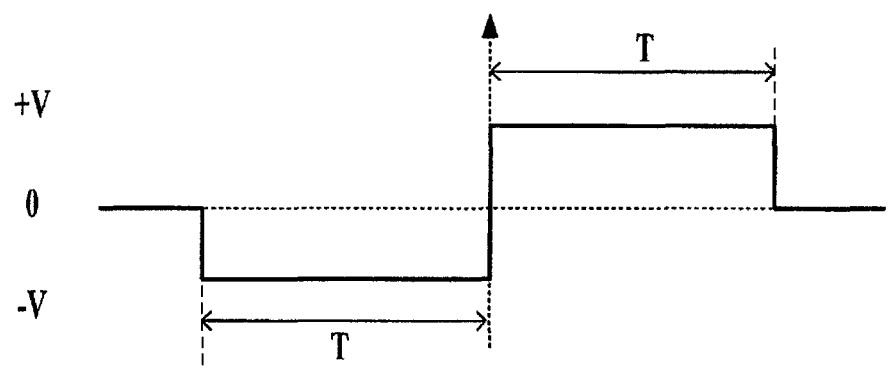
FIG. 8 is a diagram for explaining conventional waveform of a pulse signal.

Further, a transmission pulse signal as shown in FIG. 5 is generated in the embodiment. However, output timing of transmission pulse signal can be changed as shown in FIG. 7, for example. Here, arrows in FIG. 7 indicate Y axis and the center position slides by changing the parameter "t". At this time, when Fourier transform of waveform of transmission pulse signal is performed, it can be expressed as shown by the following formula (4). Here, the transmission pulse signal expressed by the following formula (4) can be expressed by the function f (x−t) wherein one cycle is 2 T. Furthermore, in the following formula (4), "ω" represents frequency, "i" represents imaginary unit and "t" indicates delay amount in time direction.

Formula 4

$$F[f(x-t_0)](\omega) = \left( e^{-i\frac{T}{2}\omega} \cdot \frac{2\sin\frac{T}{2}\omega}{\omega} - e^{i\frac{T}{2}\omega} \cdot \frac{2\sin\frac{B}{2}\omega}{\omega} + \left( e^{i\frac{A}{2}\omega} + e^{i\left(\frac{3A}{2}+B\right)\omega} \right) \cdot \frac{2\sin\frac{A}{2}\omega}{\omega} \right) \cdot e^{-i\omega t_0} \quad (4)$$

As shown in the above formula (4), in such case, the entire transmission pulse signal is to be multiplied by the coefficient "$e^{-i\omega t_0}$" as frequency characteristic. In such way, although the frequency characteristic of transmission pulse signal will receive cyclical influence by being dependent on the delay amount t, cyclical signal having a constant periodicity and having a predetermined size of amplitude with respect to the standard pulse signal is applied to the diphasic frequency response characteristic of the ultrasound probe with respect to transmission pulse signal as shown in FIG. 6, and although there will be some influence, the characteristic will be maintained potentially.

Further, in the embodiment, a transmission pulse signal is generated by setting the first pulse signal at the start of the standard pulse signal and continuously setting the second pulse signal and the first pulse signal thereafter. However, the setting positions of the first pulse signals and the second pulse signal are not limited to such positions, and the positions can be set arbitrarily to obtain a preferable frequency response characteristic.

Furthermore, the arrangement order of the first pulse signals and the second pulse signal is not limited to the above described order, and can be set arbitrarily to obtain a preferable frequency response characteristic.

Moreover, two first pulse signals and the second pulse signal do not need to be arranged continuously.

That is, two first pulse signals do not have to be arranged symmetrically along time line with respect to the second pulse signal.

The entire disclosure of Japanese Patent Application No. 2011-247363 file on Nov. 11, 2011 including description, claims, drawings, and abstract are incorporated herein by reference in its entirety.

What is claimed is:

1. An ultrasound diagnostic imaging apparatus, comprising:
    an ultrasound probe which is configured to output transmission ultrasound waves toward a subject by a driving signal and to output received signals by receiving reflection ultrasound waves from the subject;
    a transmitting circuit which is configured to output the driving signal to the ultrasound probe to generate the transmission ultrasound waves; and
    a processor which is configured to control the transmitting circuit to output the driving signal,
    wherein the processor is configured to control the transmitting circuit to output the driving signal which includes (i) a first pulse signal region of a first voltage having a pulse width A, (ii) a second pulse signal region of a second voltage, which is different from the first voltage, having a pulse width B, the second pulse signal region being adjacent to the first pulse signal region, and (iii) a third pulse signal region of the first voltage having a pulse width A+T, the third pulse signal region being adjacent to the second pulse signal region,
    where A, B and T satisfy T=2A+B, and where A>0, B>0, and T>0,
    wherein a pulse cycle is 2 T, and
    wherein the processor is configured to control the transmitting circuit to output the driving signal based on a frequency response characteristic of the ultrasound probe by setting the pulse width A and the pulse width B such that a shape of a frequency characteristic of the driving signal is substantially opposite in shape to the frequency response characteristic of the ultrasound probe in a specific frequency range.

2. The ultrasound diagnostic imaging apparatus of claim 1, wherein the processor is configured to control the transmitting circuit such that the pulse width A is smaller than the pulse width B.

3. The ultrasound diagnostic imaging apparatus of claim 1, wherein the processor is configured to control the transmitting circuit to change the pulse width A and the pulse width B.

4. The ultrasound diagnostic imaging apparatus of claim 1, wherein the driving signal is a square driving waveform which is expressed by including a formula 2, the formula 2 being:

$$F(\omega) = e^{-i\frac{T}{2}\omega} \cdot \frac{2\sin\frac{T}{2}\omega}{\omega} - e^{i\frac{T}{2}\omega} \cdot \frac{2\sin\frac{B}{2}\omega}{\omega} + \left(e^{i\frac{A}{2}\omega} + e^{i\left(\frac{3A}{2}+B\right)\omega}\right) \cdot \frac{2\sin\frac{A}{2}\omega}{\omega}$$

wherein "ω" represents a frequency and "i" represents an imaginary unit.

5. The ultrasound diagnostic imaging apparatus of claim 1, wherein:
    the first voltage has a first polarity, and
    the second voltage has a second polarity which is different from the first polarity.

6. The ultrasound diagnostic imaging apparatus of claim 1, wherein the driving signal consists of a single pulse cycle.

7. The ultrasound diagnostic imaging apparatus of claim 1, wherein the specific frequency range includes a frequency at which the frequency response characteristic of the ultrasound probe is at a peak.

8. The ultrasound diagnostic imaging apparatus of claim 1, wherein the specific frequency range includes a first range where the frequency response characteristic of the ultrasound probe cumulatively increases and a second range where the frequency response characteristic of the ultrasound probe cumulatively decreases, and the processor is configured to set the pulse width A and the pulse width B such that the frequency characteristic of the driving signal cumulatively decreases in the first range and such that the frequency characteristic of the driving signal cumulatively increases in the second range.

9. The ultrasound diagnostic imaging apparatus of claim 1, wherein the processor is configured to set the pulse width A and the pulse width B such that a shape of a frequency characteristic of the generated transmission ultrasound waves is diphasic.

10. The ultrasound diagnostic imaging apparatus of claim 9, wherein the processor is configured to set the pulse width A and the pulse width B such that positions of diphasic peaks of the frequency characteristic of the generated transmission ultrasound waves correspond to lower and higher frequency parts of the specific frequency range, respectively.

11. A method of controlling an ultrasound diagnostic imaging apparatus which is connected to an ultrasound probe which outputs transmission ultrasound waves toward a subject by a driving signal and which outputs received signals by receiving reflection ultrasound waves from the subject, the method comprising:
    generating a driving signal,
    wherein the driving signal includes (i) a first pulse signal region of a first voltage having a pulse width A, (ii) a second pulse signal region of a second voltage, which is different from the first voltage having a pulse width B, the second pulse signal region being adjacent to the first pulse signal region and (iii) a third pulse signal region of the first voltage having a pulse width A+T, the third pulse signal region being adjacent to the second pulse signal region,
    where A, B and T satisfy T=2A+B, and where A>0, B>0, and T>0,
    wherein a pulse cycle is 2 T, and
    wherein the driving signal is generated based on a frequency response characteristic of the ultrasound probe by setting the pulse width A and the pulse width B such that a shape of a frequency characteristic of the driving signal is substantially opposite in shape to the frequency response characteristic of the ultrasound probe in a specific frequency range.

12. The controlling method of claim 11, wherein generating the driving signal comprises setting a standard pulse signal in which the pulse cycle is 2 T and including an initial pulse signal region of the second voltage and having a pulse width T and a latter pulse signal region of the first voltage having the pulse width T, and setting the first pulse signal region by replacing an initial part of the initial pulse signal region of the standard pulse signal with the first pulse signal region of the first voltage having the pulse width A.

13. The control method of claim 11, wherein the pulse width A is smaller than the pulse width B.

14. The control method of claim 11, wherein the first voltage has a first polarity, and the second voltage has a second polarity which is different from the first polarity.

15. The method of claim 11, wherein the driving signal consists of a single pulse cycle.

16. The method of claim 11, wherein the specific frequency range includes a frequency at which the frequency response characteristic of the ultrasound probe is at a peak.

17. The method of claim 11, wherein the specific frequency range includes a first range where the frequency response characteristic of the ultrasound probe cumulatively increases and a second range where the frequency response characteristic of the ultrasound probe cumulatively decreases, and the pulse width A and the pulse width B are set such that the frequency characteristic of the driving signal cumulatively decreases in the first range and such that the frequency characteristic of the driving signal cumulatively increases in the second range.

18. The method of claim 11, wherein the pulse width A and the pulse width B are set such that a shape of a frequency characteristic of the generated transmission ultrasound waves is diphasic.

19. The method of claim 18, wherein the pulse width A and the pulse width B are set such that positions of diphasic peaks of the frequency characteristic of the generated transmission ultrasound waves correspond to lower and higher frequency parts of the specific frequency range, respectively.

20. The method of claim 12, wherein generating the driving signal further comprises (i) setting the second pulse signal region by replacing a second part of the initial pulse signal region of the standard pulse signal, which is adjacent to the initial part of the initial pulse signal region of the standard pulse signal at which the first pulse signal region is set, with the second pulse signal region of the second voltage having the pulse width B, and (ii) setting the third pulse signal region by replacing a third part of the initial pulse signal region of the standard pulse signal, which is adjacent to the second part thereof at which the second pulse signal region is set, with a pulse signal region of the first voltage and having the pulse width A, wherein the latter pulse signal region of the first voltage having the pulse width T is adjacent to the third part of the initial pulse signal region, such that the third pulse signal region having the pulse width A+T is set by the replacement of the third part of the initial pulse signal region with the pulse signal region of the first voltage and having the pulse width A.

* * * * *